United States Patent
Safavy

(10) Patent No.: US 8,686,190 B2
(45) Date of Patent: Apr. 1, 2014

(54) BIS-AROMATIC ANTICANCER AGENTS

(75) Inventor: Ahmad Safavy, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 542 days.

(21) Appl. No.: 12/936,608

(22) PCT Filed: Apr. 6, 2009

(86) PCT No.: PCT/US2009/039596
§ 371 (c)(1),
(2), (4) Date: Nov. 1, 2010

(87) PCT Pub. No.: WO2009/126551
PCT Pub. Date: Oct. 15, 2009

(65) Prior Publication Data
US 2011/0054037 A1      Mar. 3, 2011

Related U.S. Application Data

(60) Provisional application No. 61/043,845, filed on Apr. 10, 2008.

(51) Int. Cl.
*C07C 319/00*      (2006.01)
*C07C 321/00*      (2006.01)

(52) U.S. Cl.
USPC ........................................................ 568/47

(58) Field of Classification Search
None
See application file for complete search history.

(56) References Cited

U.S. PATENT DOCUMENTS

| | | | |
|---|---|---|---|
| 6,762,207 | B1 | 7/2004 | Reddy et al. |
| 6,767,926 | B1 | 7/2004 | Cosenza et al. |
| 7,351,434 | B2 | 4/2008 | Chern et al. |
| 2003/0114538 | A1 | 6/2003 | Reddy et al. |
| 2008/0070974 | A1 | 3/2008 | Reddy et al. |

FOREIGN PATENT DOCUMENTS

| | | |
|---|---|---|
| JP | 10-273464 | 3/1997 |
| WO | 00/59494 | 10/2000 |

OTHER PUBLICATIONS

Ballie et al., "2,-7-di-p-Chlorobenzoylnaphtho[2'3'-4:5]thiepin: a conformationally flexible new host molecule showing solvatochromic effects," CrystEngComm 6(58):326-327 (2004).
Bourdon et al., "Thiadiazepines and intermediary sulfides," Chimica Therapeutica 6(2):93-100 (1971).
Chrzaszczewska et al., "Derivatives of phenacyl sulfide," Roczniki Chemii 8:432-443 (1928).
Firestone et al., "Total synthesis of β-lactam antibiotics. VI. 3-Arylephalosporins," Journal of Organic Chemistry, 39 (23):3384-3387 (1974).
Gnanadeebam et al., "Diastereoselective Synthesis of 2,2'-Thiobis- and 2,2'-Sulfonylbis(1,3-Diarylprop-2-En-1-Ones)—An Oxidative Configurational Switch," Phosphorus, Sulfur and Silicon and the Related Elements 179 (2):203-214 (2004).
Karthikeyan et al., "Synthesis, NMR and molecular modeling study of 4,9a-diaryl-9,9a-dihydro-1H-[1,4]thiazino[4,3-a][1,3]benzimidazoles," Phosphorus, Sulfur and Silicon and the Related Elements 179(12):2561-2567 (2004).
Kretov et al., "Derivatives of phenacyl sulfides and their properties," Zhurnal Obshchei Khimii 1:396-400 (1931).
Renuga et al., "A novel four-component tandem protocol for the stereoselective synthesis of highly functionalized thiazoles," Tetrahedron 63(40):10054-10058 (2007).
Dixit et al., American Association for Cancer Research Annual Meeting, Apr. 12-16, 2008, San Diego, CA—Abstract 5683.
Sanchez-Viesca et al., "2,4,5-Trimethoxy ω-chloroacetophenone derivatives. Preparation and spectroscopic study of the new compounds," Ciencia 27(6):190-196 (1972).
Selvaraj et al., "Synthesis of some bis(aroylmethyl) sulfoxides," Indian Journal of Chemistry, Section B: Organic Chemistry Including Medicinal Chemistry, 30B(11):1060-1061 (1991).
Singh et al., "Intermediates in Hantzsch synthesis and synthesis of symmetrical thio ethers," Journal of the Indian Chemical Society 53(7):682-684 (1976).
Singh et al., "Synthesis of symmetrical α- and β-ketothioether," Indian Journal of Chemistry, 13(6):636-637 (1975).
Singh et al., "Synthesis of unsymmetrical functionalized organic sulfides," Indian Journal of Chemistry, Section B: Organic Chemistry Including Medicinal Chemistry, 24B(2): 131-136 (1985).
Valle et al., "Crystal structure of racemic 2,2'-thiobis(1-phenylethanol)" Zeitschrift fuer Kristallographie 181(1-4):95-98 (1987).
Wang, J., "Study on the reaction and mechanism for benzyl halides with sulfur under CO2(CO)8 catalysis," Xibei Shifan Daxue Xuebao, Ziran Kexueban 30(4):96-97 (1994).

*Primary Examiner* — Johann R Richter
*Assistant Examiner* — Jennifer C Sawyer
(74) *Attorney, Agent, or Firm* — Kilpatrick, Townsend & Stockton LLP

(57) ABSTRACT

Treatment of cancer includes administering a compound of formula (I) to a subject. In particular, treatment of colorectal cancer is described.

5 Claims, 1 Drawing Sheet

BIS-AROMATIC ANTICANCER AGENTS

CROSS-REFERENCE TO RELATED APPLICATIONS

This application claims priority to U.S. Provisional Application No. 61/043,845, filed Apr. 10, 2008, incorporated by reference in its entirety herein.

TECHNICAL FIELD

This disclosure relates to the treatment of cancers, for example, colorectal cancer, by methods that include administration of a bis-aromatic compound. In particular, methods of treating colorectal, pancreatic, and prostate cancers are described.

BACKGROUND

Cancer is now the second leading cause of death in the United States. In 1995, cancer accounted for 23.3% of all deaths in the United States. See, e.g., U.S. Dept. of Health and Human Services, National Center for Health Statistics, Health United States 1996-97 and *Injury Chartbook* 117 (1997).

Cancer is now primarily treated with one or a combination of three types of therapies: surgery; radiation; and chemotherapy. Surgery involves the bulk removal of diseased tissue. While surgery is sometimes effective in removing tumors located at certain sites, for example, in the breast, colon, and skin, it cannot be used in the treatment of tumors located in other areas, such as the backbone, nor in the treatment of disseminated neoplastic conditions, such as leukemia. Radiation therapy involves the exposure of living tissue to ionizing radiation causing death or damage to the exposed cells. Side effects from radiation therapy may be acute and temporary, while others may be irreversible. Chemotherapy involves the disruption of cell replication or cell metabolism. It is used most often in the treatment of breast, lung, and testicular cancer. One of the main causes of failure in this treatment of cancer is the development of drug resistance by the cancer cells, a serious problem that may lead to recurrence of disease or even death.

SUMMARY

In spite of the advances set forth above, a need continues to exist for new and more effective anticancer agents. Provided herein are bis-aromatic compounds useful in the treatment of cancer. Generically, such compounds consist of two phenyl rings linked together by a linker.

Provided herein is a method of treating cancer in a subject, the method comprising administering to the subject a therapeutically effective amount of a compound according to formula (I):

$$X\text{—}Y\text{—}Z \quad (I)$$

wherein:

Y is selected from S; S=O; $SO_2$; O; $NR^1$; $CH_2$; $(C=O)_m$; and $(COR^1)_m$;

X and Z are independently selected from:

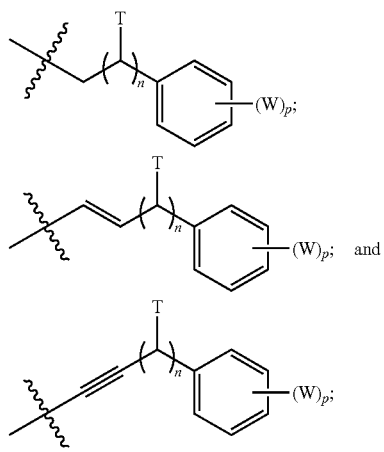

each T is independently selected from: H; $C_{1-10}$ alkyl; $OR^1$; halo; =O; $NR^1R^2$; $NO_2$; CN; $SR^1$; $SO_2$; $COOR^1$; $C_{5-12}$ cycloalkyl; $C_{5-12}$ heterocycloalkyl; $C_{5-12}$ aryl; and $C_{5-12}$ heteroaryl; wherein the alkyl, cycloalkyl, heterocycloalkyl, aryl, or heteroaryl may be substituted or unsubstituted;

each W is independently selected from: $C_{1-10}$ alkyl; $OR^1$; halo; $NR^1R^2$; $NO_2$; CN; $SR^1$; $SO_2$; $COOR^1$; $C_{5-12}$ cycloalkyl; $C_{5-12}$ heterocycloalkyl; $C_{5-12}$ aryl; and $C_{5-12}$ heteroaryl; wherein the alkyl, cycloalkyl, heterocycloalkyl, aryl, or heteroaryl may be substituted or unsubstituted;

each $R^1$ and $R^2$ is independently H or $C_{1-10}$ substituted or unsubstituted alkyl;

m is an integer from 0 to 10;

each n is independently an integer from 0 to 10; and each p is independently an integer from 0 to 5; or a pharmaceutically acceptable salt form thereof.

In some embodiments, a method of treating cancer in a subject is provided wherein the method comprises administering to the subject an effective amount of a compound according to one of formulas (II)-(VII):

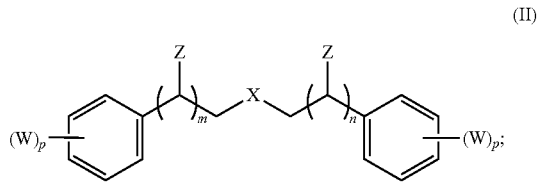

(II)

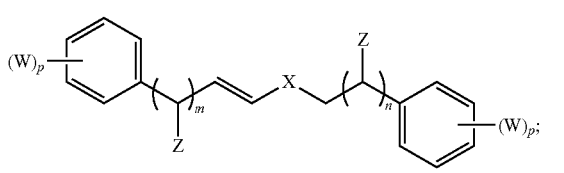

(III)

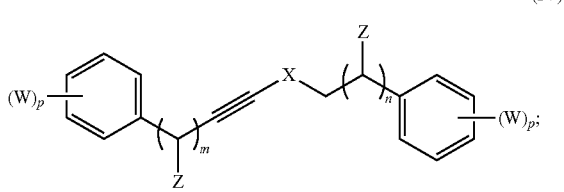

(IV)

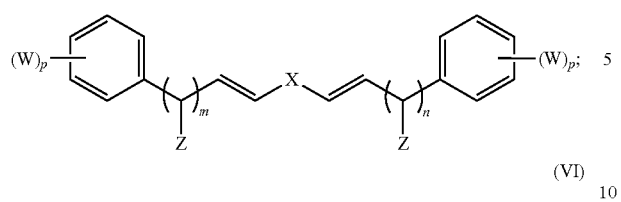
(V)

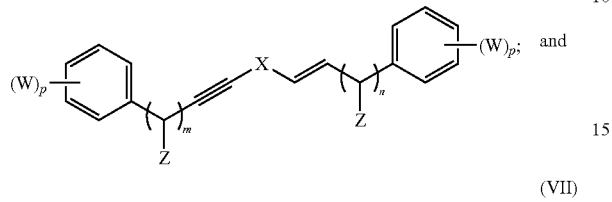
(VI)

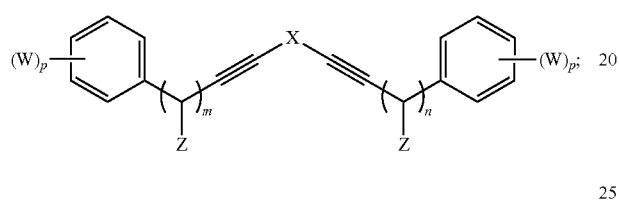
(VII)

wherein:

X is selected from: S; S=O; and SO$_2$;

each Z is independently selected from H; C$_{1-10}$ alkyl; OR$^1$; halo; =O; NR$^1$R$^2$; NO$_2$; CN; SR$^1$; SO$_2$; COOR$^1$; C$_{5-12}$ cycloalkyl; C$_{5-12}$ heterocycloalkyl; C$_{5-12}$ aryl; and C$_{5-12}$ heteroaryl; wherein the alkyl, cycloalkyl, heterocycloalkyl, aryl, or heteroaryl may be substituted or unsubstituted;

each W is independently selected from: C$_{1-10}$ alkyl; OR$^1$; halo; NR$^1$R$^2$; NO$_2$; CN; SR$^1$; SO$_2$; COOR$^1$; C$_{5-12}$ cycloalkyl; C$_{5-12}$ heterocycloalkyl; C$_{5-12}$ aryl; and C$_{5-12}$ heteroaryl; wherein the alkyl, cycloalkyl, heterocycloalkyl, aryl, or heteroaryl may be substituted or unsubstituted;

each R$^1$ and R$^2$ is independently H or C$_{1-10}$ substituted or unsubstituted alkyl;

m is independently an integer from 0 to 10;

n is independently an integer from 0 to 10; and each p is independently an integer from 0 to 5; or a pharmaceutically acceptable salt form thereof.

Non-limiting examples of compounds according to formula (II) include:

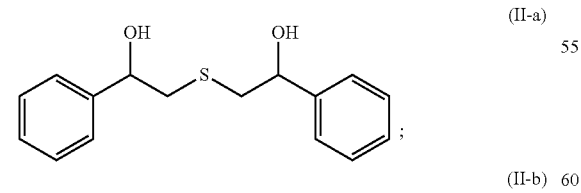
(II-a)

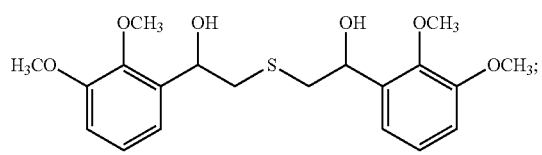
(II-b)

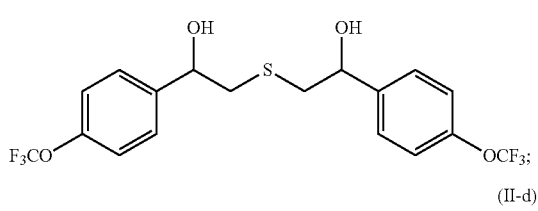
(II-c)

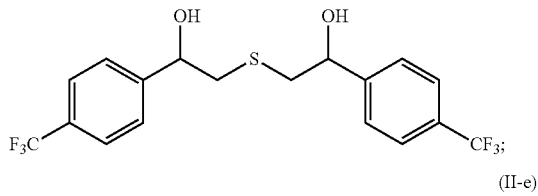
(II-d)

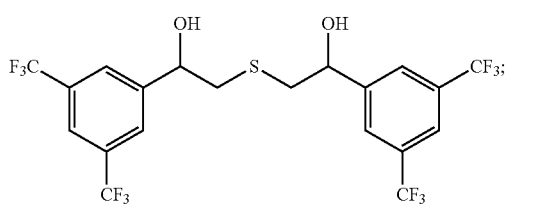
(II-e)

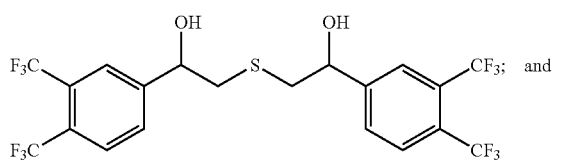
(II-f)

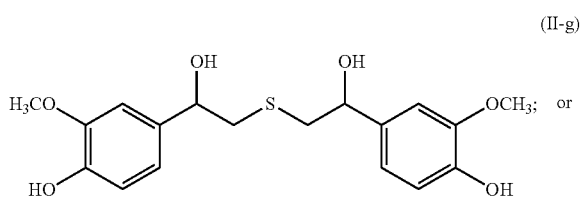
(II-g)

a pharmaceutically acceptable salt form thereof.

In some embodiments, a compound according to formula (II) is:

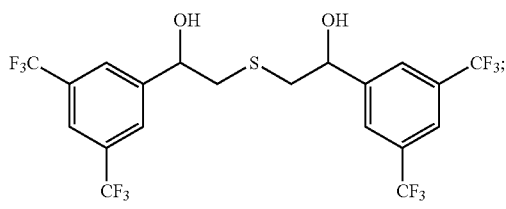 [SMILES: OC(CSCC(O)c1cc(C(F)(F)F)cc(C(F)(F)F)c1)c1cc(C(F)(F)F)cc(C(F)(F)F)c1]

or a pharmaceutically acceptable salt form thereof.

Also provided herein is a method of treating cancer in a subject, the method comprising administering a therapeutically effective amount of a compound according to one of formulas (VIII)-(XIII):

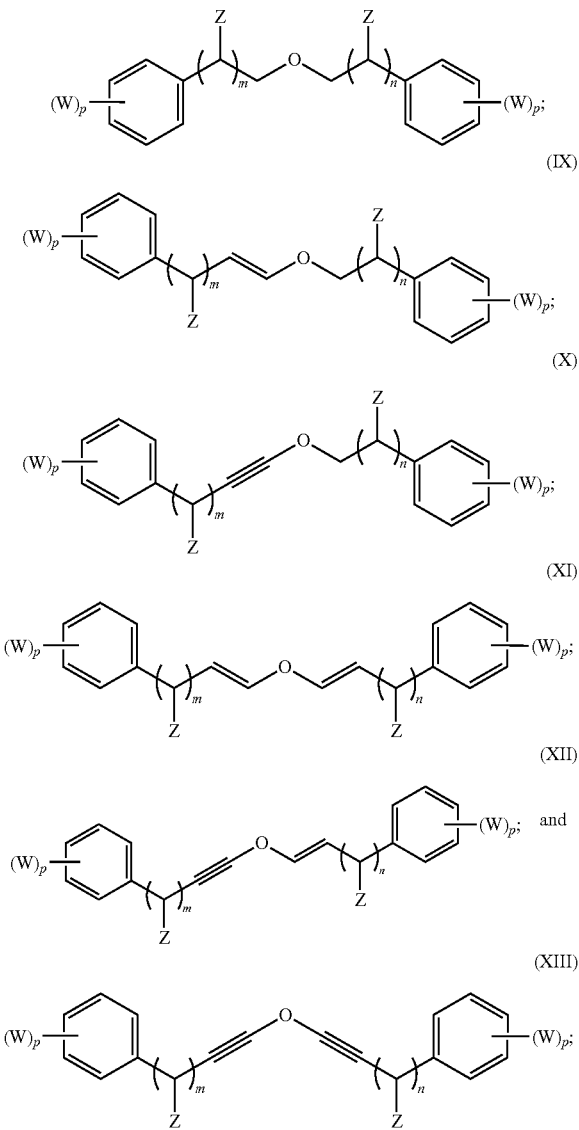

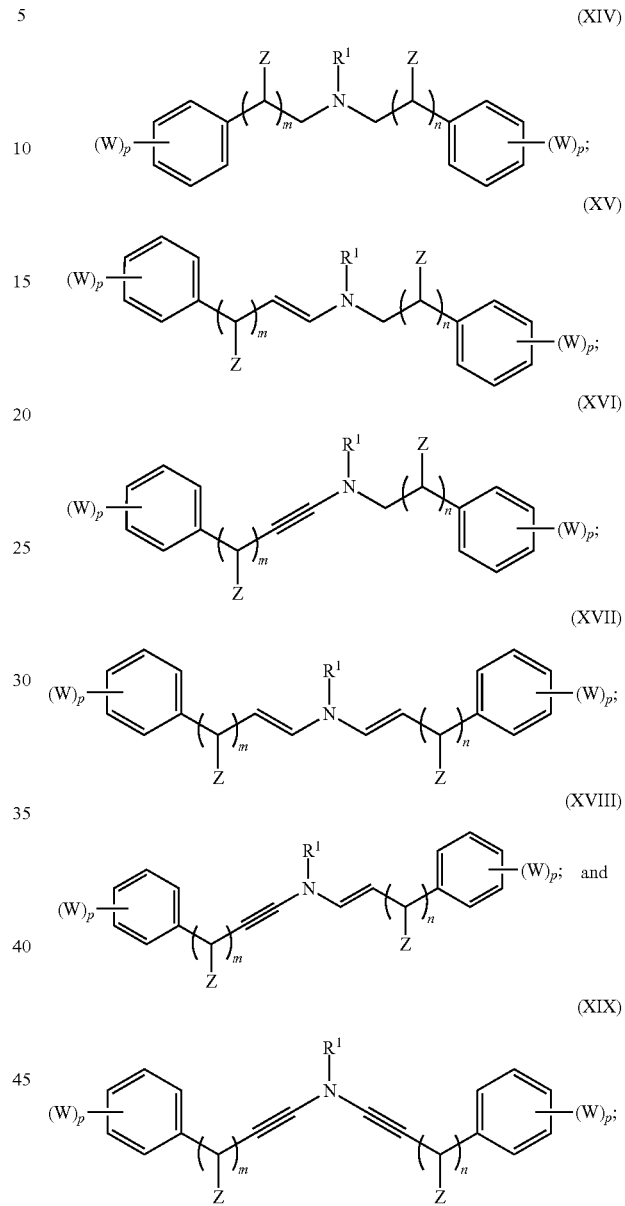

tering a therapeutically effective amount of a compound according to one of formulas (XIV)-(XIX):

wherein:
- each Z is independently selected from H; $C_{1-10}$ alkyl; $OR^1$; halo; =O; $NR^1R^2$; $NO_2$; CN; $SR^1$; $SO_2$; $COOR^1$; $C_{5-12}$ cycloalkyl; $C_{5-12}$ heterocycloalkyl; $C_{5-12}$ aryl; and $C_{5-12}$ heteroaryl; wherein the alkyl, cycloalkyl, heterocycloalkyl, aryl, or heteroaryl may be substituted or unsubstituted;
- each W is independently selected from: $C_{1-10}$ alkyl; $OR^1$; halo; $NR^1R^2$; $NO_2$; CN; $SR^1$; $SO_2$; $COOR^1$; $C_{5-12}$ cycloalkyl; $C_{5-12}$ heterocycloalkyl; $C_{5-12}$ aryl; and $C_{5-12}$ heteroaryl; wherein the alkyl, cycloalkyl, heterocycloalkyl, aryl, or heteroaryl may be substituted or unsubstituted;
- each $R^1$ and $R^2$ is independently H or $C_{1-10}$ substituted or unsubstituted alkyl;
- m is an integer from 0 to 10;
- n is an integer from 0 to 10; and
- each p is independently an integer from 0 to 5; or a pharmaceutically acceptable salt form thereof.

In some embodiments, a method of treating cancer in a subject is provided wherein the method comprises adminiswherein:
- each Z is independently selected from H; $C_{1-10}$ alkyl; $OR^1$; halo; =O; $NR^1R^2$; $NO_2$; CN; $SR^1$; $SO_2$; $COOR^1$; $C_{5-12}$ cycloalkyl; $C_{5-12}$ heterocycloalkyl; $C_{5-12}$ aryl; and $C_{5-12}$ heteroaryl; wherein the alkyl, cycloalkyl, heterocycloalkyl, aryl, or heteroaryl may be substituted or unsubstituted;
- each W is independently selected from: $C_{1-10}$ alkyl; $OR^1$; halo; $NR^1R^2$; $NO_2$; CN; $SR^1$; $SO_2$; $COOR^1$; $C_{5-12}$ cycloalkyl; $C_{5-12}$ heterocycloalkyl; $C_{5-12}$ aryl; and $C_{5-12}$ heteroaryl; wherein the alkyl, cycloalkyl, heterocycloalkyl, aryl, or heteroaryl may be substituted or unsubstituted;
- each $R^1$ and $R^2$ is independently H or $C_{1-10}$ substituted or unsubstituted alkyl;
- m is an integer from 0 to 10;

n is an integer from 0 to 10; and each p is independently an integer from 0 to 5; or a pharmaceutically acceptable salt form thereof.

Also provided herein is a method of treating cancer in a subject, the method comprising administering a therapeutically effective amount of a compound according to one of formulas (XX)-(XV):

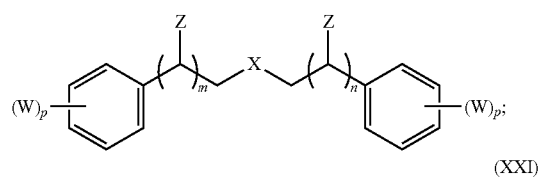

(XX)

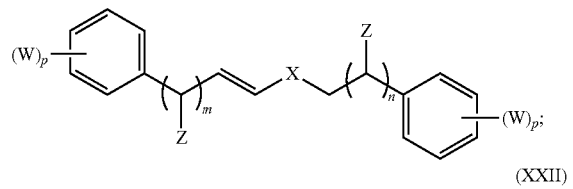

(XXI)

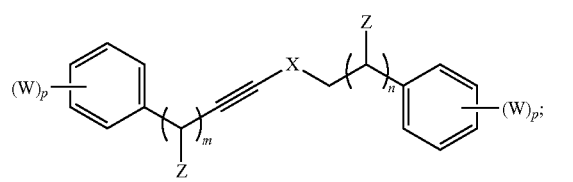

(XXII)

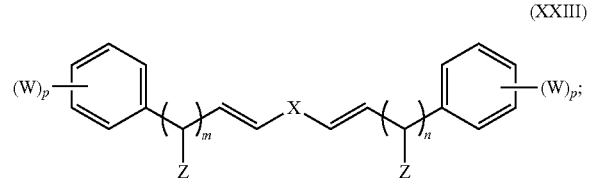

(XXIII)

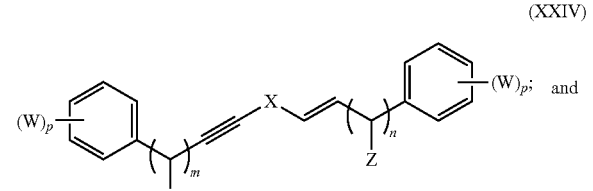

(XXIV)

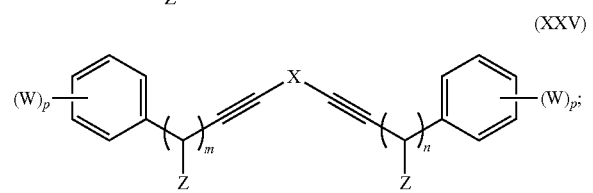

(XXV)

wherein:

X is selected from: $CH_2$; $(C=O)_k$; and $(COR^1)_k$;

each Z is independently selected from H; $C_{1-10}$ alkyl; $OR^1$; halo; $=O$; $NR^1R^2$; $NO_2$; $CN$; $SR^1$; $SO_2$; $COOR^1$; $C_{5-42}$ cycloalkyl; $C_{5-12}$ heterocycloalkyl; $C_{5-12}$ aryl; and $C_{5-12}$ heteroaryl; wherein the alkyl, cycloalkyl, heterocycloalkyl, aryl, or heteroaryl may be substituted or unsubstituted;

each W is independently selected from: $C_{1-10}$ alkyl; $OR^1$; halo; $NR^1R^2$; $NO_2$; $CN$; $SR^1$; $SO_2$; $COOR^1$; $C_{5-12}$ cycloalkyl; $C_{5-12}$ heterocycloalkyl; $C_{5-12}$ aryl; and $C_{5-12}$ heteroaryl; wherein the alkyl, cycloalkyl, heterocycloalkyl, aryl, or heteroaryl may be substituted or unsubstituted;

each $R^1$ and $R^2$ is independently H or $C_{1-10}$ substituted or unsubstituted alkyl;

k is an integer from 0 to 10;

m is an integer from 0 to 10;

n is an integer from 0 to 10; and each p is independently an integer from 0 to 5; or a pharmaceutically acceptable salt form thereof.

For the above methods, in some embodiments, the subject is a human.

In some embodiments of the above methods, the cancer is selected from: bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. In some embodiments, the cancer is colorectal cancer. In some embodiments, the cancer is pancreatic cancer. In some embodiments, the cancer is prostate cancer.

Further provided herein is a method of promoting cell death in a cell, the method comprising contacting the cell with a therapeutically effective amount of a compound of formula (I), or a pharmaceutically acceptable salt form thereof.

Also provided herein is a pharmaceutical composition comprising one or more of a pharmaceutically acceptable carrier, excipient, diluent, or adjuvant; and a compound according to formula (I), or a pharmaceutically acceptable salt form thereof. In some embodiments, the carrier, excipient, or diluent is a physiologically acceptable saline solution. In some embodiments, the composition further comprises a pain relief agent, an antinausea agent, or an additional anticancer agent.

Provided herein is a compound according to one or more of the following:

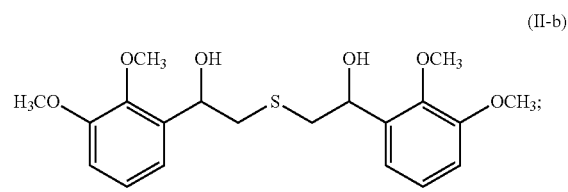

(II-b)

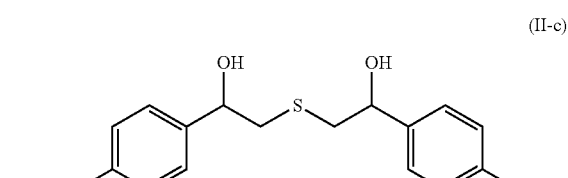

(II-c)

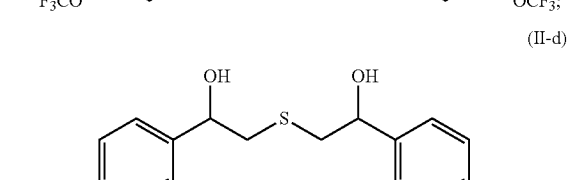

(II-d)

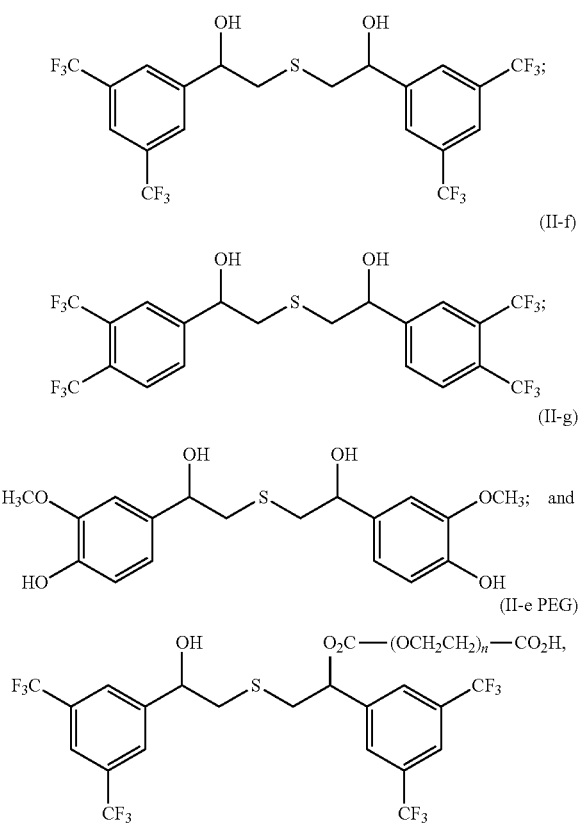

wherein n is an integer from 1 to 1000;
or a pharmaceutically acceptable salt form thereof.

Further provided herein is a pharmaceutical composition comprising one or more of a pharmaceutically acceptable carrier, excipient, diluent, or adjuvant; and a compound according to one or more of formulas (II-b), (II-c), (II-d), (II-e), (II-f), (II-g), and (II-e PEG).

The details of one or more embodiments of the invention are set forth in the accompanying drawings and the description below. Other features, objects, and advantages of the invention will be apparent from the description and drawings, and from the claims.

DETAILED DESCRIPTION

I. Definitions

Figure 1:
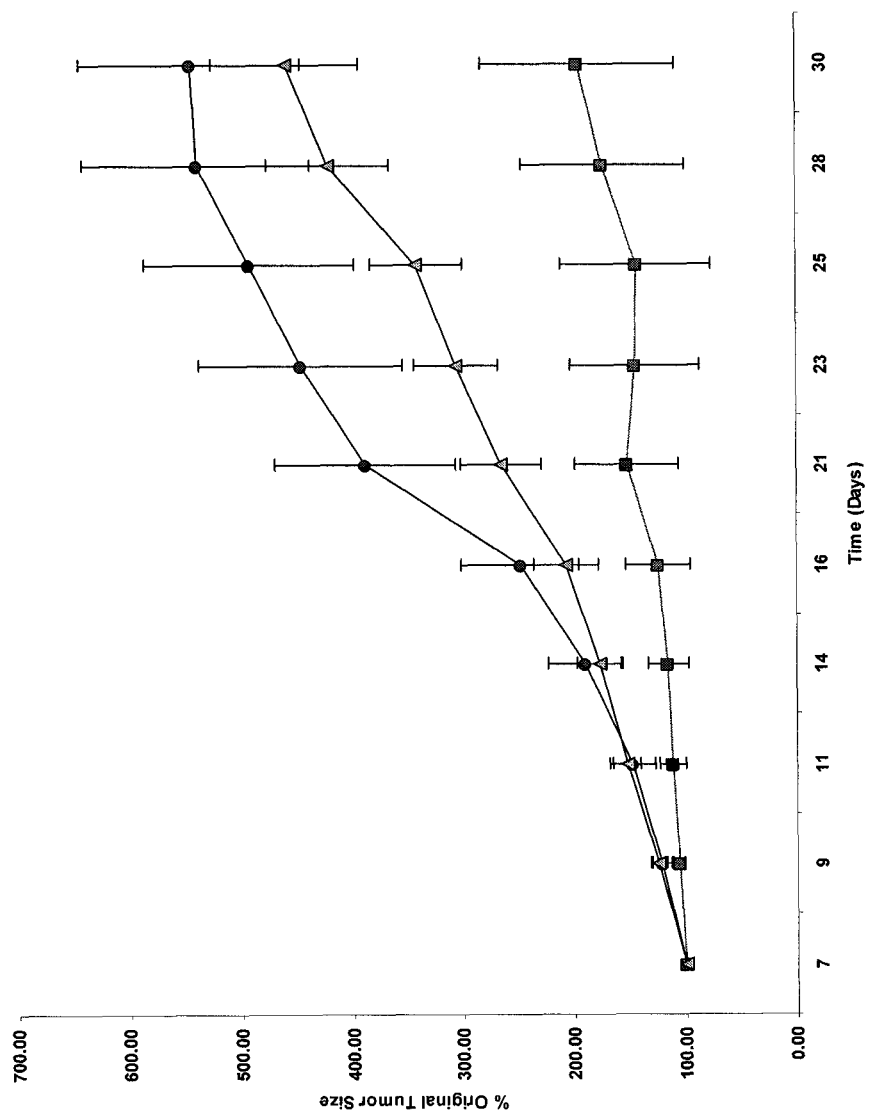
FIG. 1 illustrates antitumor activity of compound II-e in nude mice bearing LS174-T human colon carcinoma tumors.

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, "administration" refers to delivery of a compound of formula (I) by any external route, including, without limitation, IV, intramuscular, SC, intranasal, inhalation, transdermal, oral, rectal, sublingual, and parenteral administration.

The term "contacting" means bringing at least two moieties together, whether in an in vitro system or an in vivo system.

The expression "effective amount," when used to describe an amount of compound applied in a method, refers to the amount of a compound that achieves the desired pharmacological effect or other effect, for example an amount that slows abnormal growth or proliferation, or induces death of cancer cells, resulting in a useful effect.

The terms "treating" and "treatment" mean causing a therapeutically beneficial effect, such as ameliorating existing symptoms, preventing additional symptoms, ameliorating or preventing the underlying metabolic causes of symptoms, postponing or preventing the further development of a disorder, and/or reducing the severity of symptoms that will or are expected to develop.

As used herein, "subject" (as in the subject of the treatment) means both mammals and non-mammals. Mammals include, for example, humans; non-human primates, e.g. apes and monkeys; cattle; horses; sheep; rats; mice; pigs; and goats. Non-mammals include, for example, fish and birds.

The term "alkyl," by itself or as part of another substituent, means, unless otherwise stated, a straight or branched chain, which may be fully saturated, mono- or polyunsaturated, can include di- and multivalent radicals, and can have a number of carbon atoms optionally designated (i.e., $C_1$-$C_8$ means one to eight carbons). Examples of saturated hydrocarbon groups include, but are not limited to, groups such as methyl, ethyl, n-propyl, isopropyl, n-butyl, t-butyl, isobutyl, sec-butyl, n-pentyl, isopentyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotonyl, 2-isopentenyl, 2-(butadienyl), 2,4-pentadienyl, 3-(1,4-pentadienyl), ethynyl, 1- and 3-propynyl, 3-butynyl, and higher homologs and isomers.

The term "alkoxy" is used in its conventional sense, and refers to those alkyl groups attached to the remainder of the molecule via an oxygen atom. Alkoxy groups include, but are not limited to, methoxy, ethoxy, isopropoxy, trifluoromethoxy, and difluoromethoxy.

The term "cycloalkyl", by itself or in combination with other terms, represents, unless otherwise stated, cyclic versions of substituted or unsubstituted "alkyl". Examples of cycloalkyl groups include, but are not limited to, cyclopentyl, cyclohexyl, 1-cyclohexenyl, 3-cyclohexenyl, cycloheptyl, and the like. The carbon atoms of the cyclic structures are optionally oxidized.

The term "heterocycloalkyl" as used herein refers to a cycloalkyl having a heteroatom. The heteroatom can occupy any position, including the position at which the heterocycle is attached to the remainder of the molecule. Examples of heterocycloalkyl groups include, but are not limited to, pyrrolidinyl, 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, dihydroimidazolyl, benzoimidazolyl, dihydrooxazolyl, and the like. The heteroatoms and carbon atoms of the cyclic structures are optionally oxidized or, in the case of N, quaternized.

The terms "halo" or "halogen," by themselves or as part of another substituent, mean, unless otherwise stated, a fluorine, chlorine, bromine, or iodine atom.

The term "aryl" means, unless otherwise stated, a polyunsaturated, aromatic, hydrocarbon moiety which can be a single ring or multiple rings (e.g., from 1 to 3 rings) which are fused together or linked covalently. The term "heteroaryl" refers to aryl groups (or rings) that contain from one to four heteroatoms selected from N, O, and S, wherein the nitrogen, carbon and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. "Aryl" and "heteroaryl" also encompass ring systems in which one or more non-aromatic ring systems are fused, or otherwise bound, to an aryl or heteroaryl system. Aryl-containing groups include, but are not limited to, phenyl, phenoxycarbonyl, benzoyl, benzyl, phenylpiperidinyl, phenylmorpholinyl, and dihydrobenzodioxyl (e.g., N,N-dihydrobenzodioxyl).

As used herein, "substituted" or "optionally substituted" refers to substitution by one or more substituents, in some embodiments one, two, three, or four substituents. In some embodiments, two substituents may join to form a cyclic or heterocyclic ring containing 3-7 atoms. Non-limiting examples of substituents include $C_{1-10}$ alkyl; $OR^1$; halo; $NR^1R^2$; $NO_2$; $CN$; $SR^1$; $SO_2$; $COOR^1$; $C_{5-12}$ cycloalkyl; $C_{5-12}$ heterocycloalkyl; $C_{5-12}$ aryl; and $C_{5-12}$ heteroaryl; wherein the alkyl, cycloalkyl, heterocycloalkyl, aryl, or heteroaryl may be substituted or unsubstituted, wherein each $R^1$ and $R^2$ is independently H or $C_{1-10}$ substituted or unsubstituted alkyl. In some embodiments, a substituent is selected from $C_{1-6}$ alkyl, halo, and $OR^1$.

As used herein, the term "heteroatom" includes oxygen (O), nitrogen (N), sulfur and (S).

II. Compositions

Provided herein are bis-aromatic compounds having two phenyl rings linked together by a linker. In some embodiments, the linker is a hydrocarbon linker. In some embodiments, the linker is a hydrocarbon linker having one or more heteroatoms intercalated in the chain (e.g., S, N, and O). In some embodiments, the linker contains one or more sites of unsaturation. In some embodiments, the linker is substituted (e.g., substituted by a ketone, hydroxy, or alkoxy moiety). In some embodiments, the two phenyl rings are independently substituted or unsubstituted. In some embodiments, the two phenyl rings are independently substituted by one or more of an alkyl, alkoxy, haloalkyl, or haloalkoxy moiety. In some embodiments, the two phenyl rings are the same. In some embodiments, the two phenyl rings are different.

Provided herein are compounds having formula (I):

$$X—Y—Z \quad (I)$$

wherein:

Y is selected from S; S=O; $SO_2$; O; $NR^1$; $CH_2$; $(C=O)_m$; and $(COR^1)_m$;

X and Z are independently selected from:

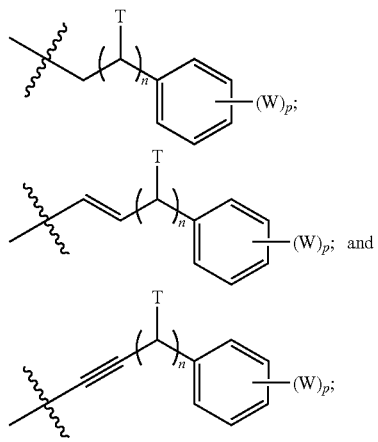

each T is independently selected from: H; $C_{1-10}$ alkyl; $OR^1$; halo; =O; $NR^1R^2$; $NO_2$; CN; $SR^1$; $SO_2$; $COOR^1$; $C_{5-12}$ cycloalkyl; $C_{5-12}$ heterocycloalkyl; $C_{5-12}$ aryl; and $C_{5-12}$ heteroaryl, wherein the alkyl, cycloalkyl, heterocycloalkyl, aryl, or heteroaryl may be substituted or unsubstituted;

each W is independently selected from: $C_{1-10}$ alkyl; $OR^1$; halo; $NR^1R^2$; $NO_2$; CN; $SR^1$; $SO_2$; $COOR^1$; $C_{5-12}$ cycloalkyl; $C_{5-12}$ heterocycloalkyl; $C_{5-12}$ aryl; and $C_{5-12}$ heteroaryl, wherein the alkyl, cycloalkyl, heterocycloalkyl, aryl, or heteroaryl may be substituted or unsubstituted;

each $R^1$ and $R^2$ is independently H or $C_{1-10}$ substituted or unsubstituted alkyl;

m is an integer from 0 to 10;

each n is independently an integer from 0 to 10; and each p is independently an integer from 0 to 5; or a pharmaceutically acceptable salt form thereof.

In some embodiments, Y is selected from S; S=O; $SO_2$; O; $NR^1$; $(C=O)_m$; and $(COR^1)_m$. In some embodiments, Y is S. In some embodiments, T is selected from =O and $OR^1$. In some embodiments, T is OH. In some embodiments, X and Z are the same. In some embodiments, X and Z are different. In some embodiments, X and Z are

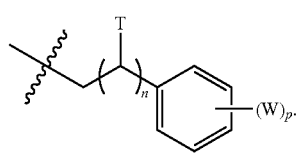

In some embodiments, both rings are substituted identically. In some embodiments, each W is independently selected from $C_{1-10}$ alkyl and $OR^1$. In some embodiments, each W is independently selected from $CF_3$, OH, $OCH_3$, and $OCF_3$. In some embodiments, p is 2 and W is $OCH_3$ and located at the ortho and meta positions on the ring. In some embodiments, p is 1 and W is $OCF_3$ and located at the para position on the ring. In some embodiments, p is 1 and W is $CF_3$ and located at the para position on the ring. In some embodiments, p is 2 and W is $CF_3$ and located at the meta positions on the ring. In some embodiments, p is 2 and W is $OCH_3$, located in the meta position on the ring, and OH, located in the para position on the ring. In some embodiments, each n is an integer from 0 to 5. In some embodiments, each n is 1. In some embodiments, each p is an integer from 1 to 3. In some embodiments, each p is 2. In some embodiments, each p is 1.

In some embodiments, a compound according to formula (I) is a compound according to one of formulas (II)-(VII):

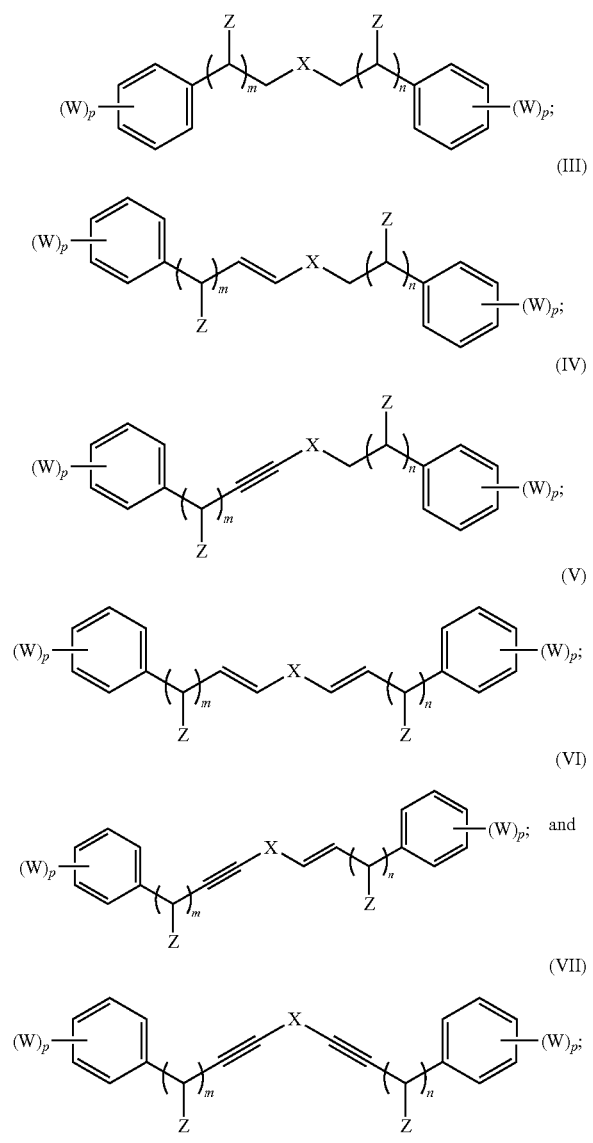

wherein:
X is selected from: S; S=O; and SO$_2$;
each Z is independently selected from H; C$_{1-10}$ alkyl; OR$^1$; halo; =O; NR$^1$R$^2$; NO$_2$; CN; SR$^1$; SO$_2$; COOR$^1$; C$_{5-12}$ cycloalkyl; C$_{5-12}$ heterocycloalkyl; C$_{5-12}$ aryl; and C$_{5-12}$ heteroaryl; wherein the alkyl, cycloalkyl, heterocycloalkyl, aryl, or heteroaryl may be substituted or unsubstituted;
each W is independently selected from: C$_{1-10}$ alkyl; OR$^1$; halo; NR$^1$R$^2$; NO$_2$; CN; SR$^1$; SO$_2$; COOR$^1$; C$_{5-12}$ cycloalkyl; C$_{5-12}$ heterocycloalkyl; C$_{5-12}$ aryl; and C$_{5-12}$ heteroaryl; wherein the alkyl, cycloalkyl, heterocycloalkyl, aryl, or heteroaryl may be substituted or unsubstituted;
each R$^1$ and R$^2$ is independently H or C$_{1-10}$ substituted or unsubstituted alkyl;
m is an integer from 0 to 10;
n is an integer from 0 to 10; and
each p is independently an integer from 0 to 5; or
a pharmaceutically acceptable salt form thereof.

In some embodiments, Z is selected from =O and OR$^1$. In some embodiments, Z is OH. In some embodiments, both rings are substituted identically. In some embodiments, each W is independently selected from C$_{1-10}$ alkyl and OR$^1$. In some embodiments, each W is independently selected from CF$_3$, OH, OCH$_3$, and OCF$_3$. In some embodiments, p is 2 and W is OCH$_3$ and located at the ortho and meta positions on the ring. In some embodiments, p is 1 and W is OCF$_3$ and located at the para position on the ring. In some embodiments, p is 1 and W is CF$_3$ and located at the para position on the ring. In some embodiments, p is 2 and W is CF$_3$ and located at the meta positions on the ring. In some embodiments, p is 2 and W is OCH$_3$, located in the meta position on the ring, and OH, located in the para position on the ring. In some embodiments, n is an integer from 0 to 5. In some embodiments, n is 1. In some embodiments, m is an integer from 0 to 5. In some embodiments, m is 1. In some embodiments, each p is an integer from 1 to 3. In some embodiments, each p is 2. In some embodiments, each p is 1.

Non-limiting examples of a compound according to formula (II) include:

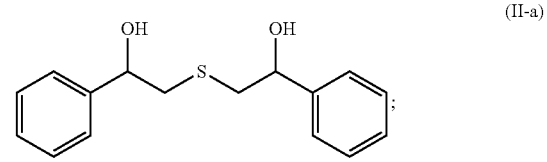

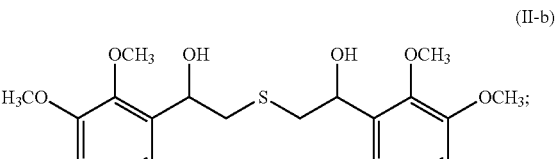

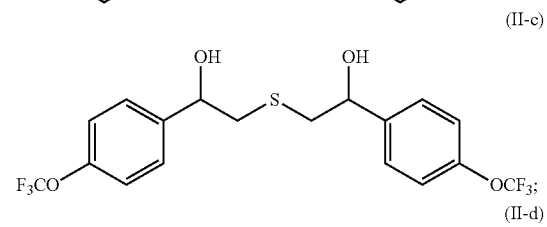

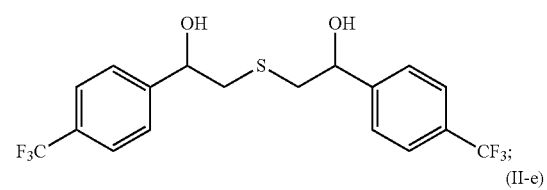

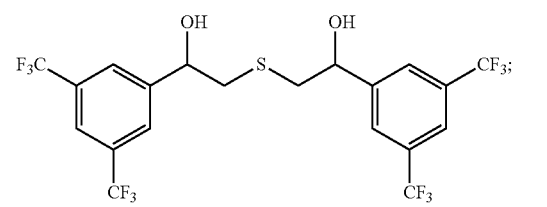

-continued (II-f)
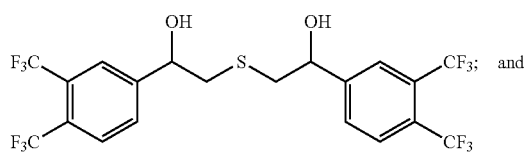

and (II-g)
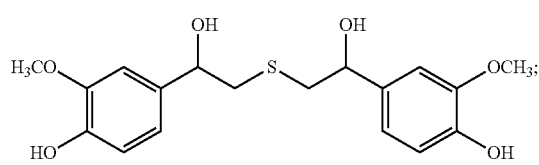

or a pharmaceutically acceptable salt form thereof.

In some embodiments, a compound according to formula (I) is a compound according to one of formulas (VIII)-(XIII):

(VIII)
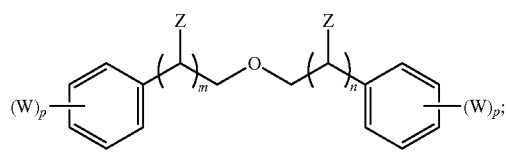

(IX)
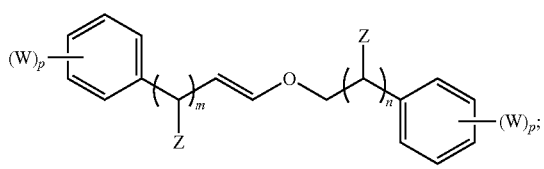

(X)
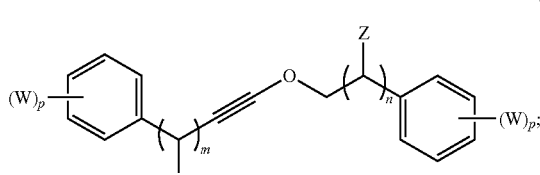

(XI)
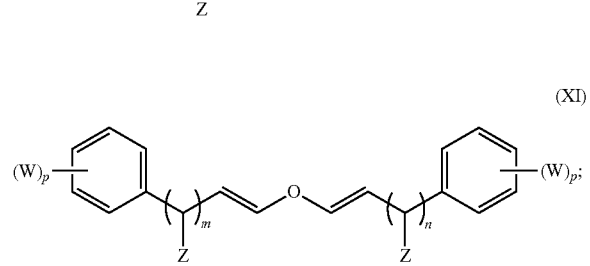

(XII)
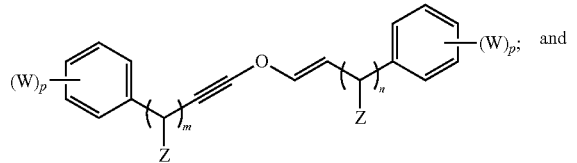
and (XIII)
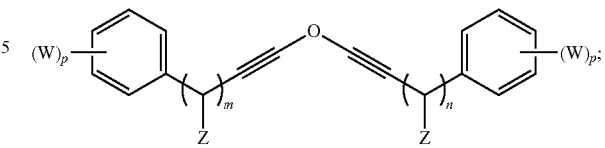

wherein:
- each Z is independently selected from H; $C_{1-10}$ alkyl; $OR^1$; halo; =O; $NR^1R^2$; $NO_2$; CN; $SR^1$; $SO_2$; $COOR^1$; $C_{5-12}$ cycloalkyl; $C_{5-12}$ heterocycloalkyl; $C_{5-12}$ aryl; and $C_{5-12}$ heteroaryl; wherein the alkyl, cycloalkyl, heterocycloalkyl, aryl, or heteroaryl may be substituted or unsubstituted;
- each W is independently selected from: $C_{1-10}$ alkyl; $OR^1$; halo; $NR^1R^2$; $NO_2$; CN; $SR^1$; $SO_2$; $COOR^1$; $C_{5-12}$ cycloalkyl; $C_{5-12}$ heterocycloalkyl; $C_{5-12}$ aryl; and $C_{5-12}$ heteroaryl; wherein the alkyl, cycloalkyl, heterocycloalkyl, aryl, or heteroaryl may be substituted or unsubstituted;
- each $R^1$ and $R^2$ is independently H or $C_{1-10}$ substituted or unsubstituted alkyl;
- m is an integer from 0 to 10;
- n is an integer from 0 to 10; and
- each p is independently an integer from 0 to 5; or a pharmaceutically acceptable salt form thereof.

In some embodiments, Z is selected from =O and $OR^1$. In some embodiments, Z is OH. In some embodiments, both rings are substituted identically. In some embodiments, each W is independently selected from $C_{1-10}$ alkyl and $OR^1$. In some embodiments, each W is independently selected from $CF_3$, OH, $OCH_3$, and $OCF_3$. In some embodiments, p is 2 and W is $OCH_3$ and located at the ortho and meta positions on the ring. In some embodiments, p is 1 and W is $OCF_3$ and located at the para position on the ring. In some embodiments, p is 1 and W is $CF_3$ and located at the para position on the ring. In some embodiments, p is 2 and W is $CF_3$ and located at the meta positions on the ring. In some embodiments, p is 2 and W is $OCH_3$, located in the meta position on the ring, and OH, located in the para position on the ring. In some embodiments, n is an integer from 0 to 5. In some embodiments, n is 1. In some embodiments, m is an integer from 0 to 5. In some embodiments, m is 1. In some embodiments, each p is an integer from 1 to 3. In some embodiments, each p is 2. In some embodiments, each p is 1.

In some embodiments, a compound according to formula (I) is a compound according to one of formulas (XIV)-(XIX):

(XIV)
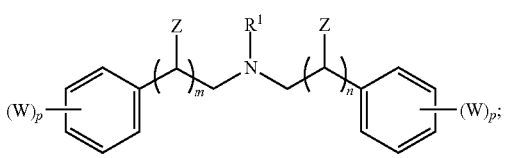

-continued

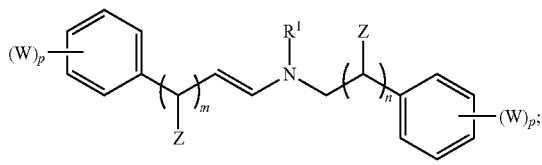
(XV)

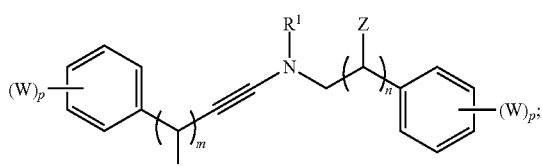
(XVI)

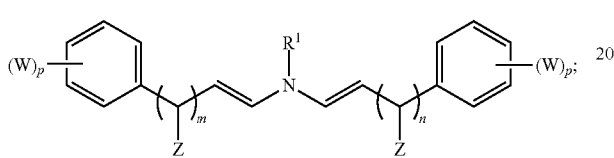
(XVII)

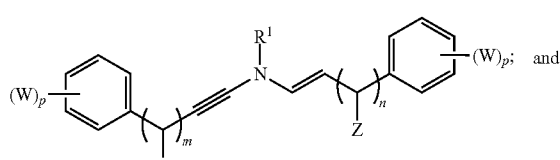
(XVIII)

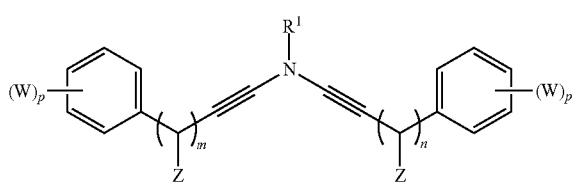
(XIX)

wherein:
- each Z is independently selected from H; $C_{1-10}$ alkyl; $OR^1$; halo; =O; $NR^1R^2$; $NO_2$; CN; $SR^1$; $SO_2$; $COOR^1$; $C_{5-12}$ cycloalkyl; $C_{5-12}$ heterocycloalkyl; $C_{5-12}$ aryl; and $C_{5-12}$ heteroaryl; wherein the alkyl, cycloalkyl, heterocycloalkyl, aryl, or heteroaryl may be substituted or unsubstituted;
- each W is independently selected from: $C_{1-10}$ alkyl; $OR^1$; halo; $NR^1R^2$; $NO_2$; CN; $SR^1$; $SO_2$; $COOR^1$; $C_{5-12}$ cycloalkyl; $C_{5-12}$ heterocycloalkyl; $C_{5-12}$ aryl; and $C_{5-12}$ heteroaryl; wherein the alkyl, cycloalkyl, heterocycloalkyl, aryl, or heteroaryl may be substituted or unsubstituted;
- each $R^1$ and $R^2$ is independently H or $C_{1-10}$ substituted or unsubstituted alkyl;
- m is an integer from 0 to 10;
- n is an integer from 0 to 10; and
- each p is independently an integer from 0 to 5; or
- a pharmaceutically acceptable salt form thereof.

In some embodiments, Z is selected from =O and $OR^1$. In some embodiments, Z is OH. In some embodiments, both rings are substituted identically. In some embodiments, each W is independently selected from $C_{1-10}$ alkyl and $OR^1$. In some embodiments, each W is independently selected from $CF_3$, OH, $OCH_3$, and $OCF_3$. In some embodiments, p is 2 and W is $OCH_3$ and located at the ortho and meta positions on the ring. In some embodiments, p is 1 and W is $OCF_3$ and located at the para position on the ring. In some embodiments, p is 1 and W is $CF_3$ and located at the para position on the ring. In some embodiments, p is 2 and W is $CF_3$ and located at the meta positions on the ring. In some embodiments, p is 2 and W is $OCH_3$, located in the meta position on the ring, and OH, located in the para position on the ring. In some embodiments, n is an integer from 0 to 5. In some embodiments, n is 1. In some embodiments, m is an integer from 0 to 5. In some embodiments, m is 1. In some embodiments, each p is an integer from 1 to 3. In some embodiments, each p is 2. In some embodiments, each p is 1.

In some embodiments, a compound according to formula (I) is a compound according to one of formulas (XX)-(XXV):

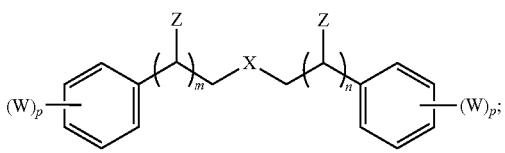
(XX)

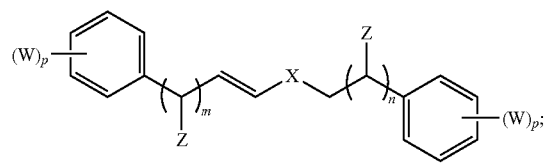
(XXI)

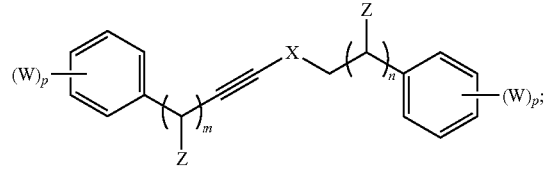
(XXII)

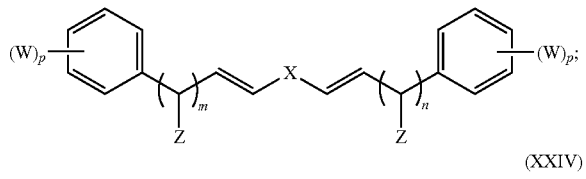
(XXIII)

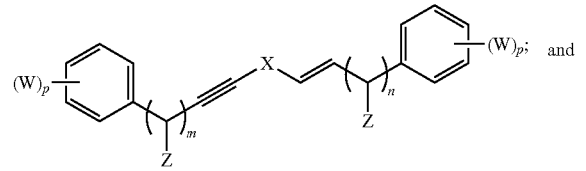
(XXIV)

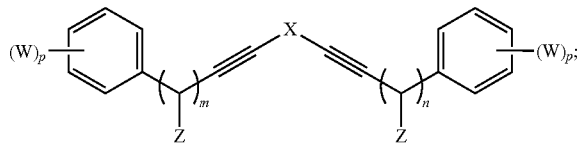
(XXV)

wherein:
- X is selected from: $CH_2$; $(C=O)_k$; and $(COR^1)_k$;
- each Z is independently selected from H; $C_{1-10}$ alkyl; $OR^1$; halo; =O; $NR^1R^2$; $NO_2$; CN; $SR^1$; $SO_2$; $COOR^1$; $C_{5-12}$ cycloalkyl; $C_{5-12}$ heterocycloalkyl; $C_{5-12}$ aryl; and $C_{5-12}$ heteroaryl; wherein the alkyl, cycloalkyl, heterocycloalkyl, aryl, or heteroaryl may be substituted or unsubstituted;

each W is independently selected from: $C_{1-10}$ alkyl; $OR^1$; halo; $NR^1R^2$; $NO_2$; CN; $SR^1$; $SO_2$; $COOR^1$; $C_{5-12}$ cycloalkyl; $C_{5-12}$ heterocycloalkyl; $C_{5-12}$ aryl; and $C_{5-12}$ heteroaryl; wherein the alkyl, cycloalkyl, heterocycloalkyl, aryl, or heteroaryl may be substituted or unsubstituted;

each $R^1$ and $R^2$ is independently H or $C_{1-10}$ substituted or unsubstituted alkyl;

k is an integer from 0 to 10;

m is an integer from 0 to 10;

n is an integer from 0 to 10; and each p is independently an integer from 0 to 5;

or a pharmaceutically acceptable salt form thereof.

In some embodiments, X is selected from $(C=O)_k$ and $(COR^1)_k$. In some embodiments, X is OH. In some embodiments, Z is selected from =O and $OR^1$. In some embodiments, Z is OH. In some embodiments, both rings are substituted identically. In some embodiments, each W is independently selected from $C_{1-10}$ alkyl and $OR^1$. In some embodiments, each W is independently selected from $CF_3$, OH, $OCH_3$, and $OCF_3$. In some embodiments, p is 2 and W is $OCH_3$ and located at the ortho and meta positions on the ring. In some embodiments, p is 1 and W is $OCF_3$ and located at the para position on the ring. In some embodiments, p is 1 and W is $CF_3$ and located at the para position on the ring. In some embodiments, p is 2 and W is $CF_3$ and located at the meta positions on the ring. In some embodiments, p is 2 and W is $OCH_3$, located in the meta position on the ring, and OH, located in the para position on the ring. In some embodiments, k is an integer from 0 to 5. In some embodiments, k is 1. In some embodiments, n is an integer from 0 to 5. In some embodiments, n is 1. In some embodiments, m is an integer from 0 to 5. In some embodiments, m is 1. In some embodiments, each p is an integer from 1 to 3. In some embodiments, each p is 2. In some embodiments, each p is 1.

The term "pharmaceutically acceptable salt" refers to salts which possess toxicity profiles within a range that affords utility in pharmaceutical applications. Pharmaceutically unacceptable salts may nonetheless possess properties such as high crystallinity, which may render them useful, for example in processes of synthesis, purification or formulation of compounds described herein. In general, the useful properties of the compounds described herein do not depend critically on whether the compound is or is not in a salt form, so unless clearly indicated otherwise (such as specifying that the compound should be in "free base" or "free acid" form), reference in the specification to a compound of formula (I) should be understood as encompassing salt forms of the compound, whether or not this is explicitly stated.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts.

All of these salts may be prepared by conventional means from the corresponding compound according to formula (I) by reacting, for example, the appropriate acid or base with a compound according to formula (I). Preferably the salts are in crystalline form, and preferably prepared by crystallization of the salt from a suitable solvent. A person skilled in the art will know how to prepare and select suitable salt forms for example, as described in *Handbook of Pharmaceutical Salts: Properties, Selection, and Use* By P. H. Stahl and C. G. Wermuth (Wiley-VCH 2002).

In some embodiments, a compound of formula (I) can be conjugated at any suitable position to a water-solubilizing moiety. Non-limiting examples of such moieties include poly (ethylene glycol) (PEG), PEG derivatives, such as amino or hydroxyl reactive PEG, biotin PEG, and functionalized PEG (e.g., PEG functionalized with amino, carboxylic, thiol, azide, or silane moieties), poly(amino acids), peptides and proteins, and carbohydrates. In some embodiments, a linker can be used to link the moiety to a compound of formula (I). In some embodiments, compound II-e can be conjugated to a PEG moiety. For example, compound II-e can be coupled to PEG disuccinate (SX-PEG-SX) using EDC as a coupling agent and DMAP as a catalyst. The conjugate can then be purified by size-exclusion chromatography or dialysis. Non-limiting examples of such compounds include:

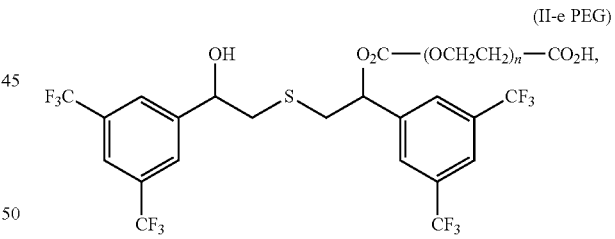

(II-e PEG)

wherein n is an integer from 1 to 1000; or a pharmaceutically acceptable salt form thereof.

The compounds according to formula (I), and salts thereof as well as intermediates used in making compounds according to formula (I), and salts thereof, may be administered in the form of prodrugs. By "prodrug" is meant, for example, any compound (whether itself active or inactive) that is converted chemically in vivo into a biologically active compound of the formula (I) following administration of the prodrug to a subject.

Generally a "prodrug" is a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds according to formula (I).

The suitability and techniques involved in making and using prodrugs are well known by those skilled in the art. Preparation and use of prodrugs is discussed in T. Higuchi and V. Stella, "Pro-drugs as Novel Delivery Systems," Vol. 14 of the ACS Symposium Series, and in Bioreversible Carriers in Drug Design, ed. Edward B. Roche, American Pharmaceutical Association and Pergamon Press, 1987, both of which are hereby incorporated by reference in their entirety.

III. Methods of Making

The compounds described herein can be synthesized using conventional techniques using readily available starting materials. For example, a compound of formula (I) can be obtained via standard organic chemistry synthesis methods, see, for example, Example 1. In some embodiments, compounds according to formula (I) can be prepared using the following synthetic protocol, wherein R is a substituted or unsubstituted aryl group.

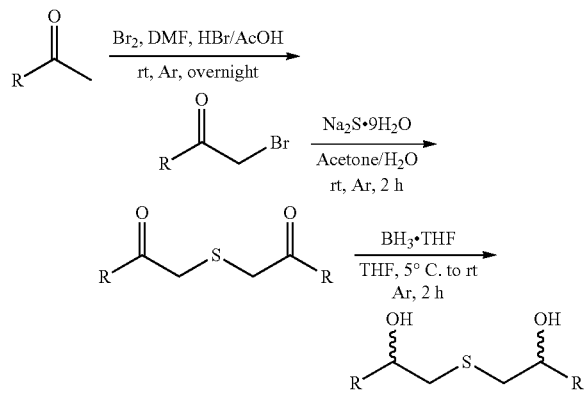

Bromoacetophenones, either from a commercial source or synthesized by direct bromination of the corresponding acetophenones, can be used. The bromination can be affected by treating a solution of the acetophenone in dry DMF with elemental bromine in the same solvent and initiating the reaction with catalytic amounts of HBr in acetic acid. The solution can then be stirred at 37° C. overnight, the solvent distilled in vacuum, and the residue purified by column chromatography on silica gel using a 1:1 mixture of hexanes in ethyl acetate. The bromoacetophenones can then be dissolved in acetone containing a catalytic amount of sodium iodide and the solution treated with finely pulverized sodium sulfate. The resulting heterogeneous mixture can then be vigorously stirred at room temperature overnight. The precipitated solid can be filtered off and the acetone distilled in vacuum. The oily residue can be purified by silica gel chromatography using ethyl acetate-graduated hexanes. The resulting diketo product can then be reduced to the corresponding diol with diborane at ambient temperature.

It will be appreciated by one skilled in the art that the processes described herein are not the exclusive means by which the compounds described herein may be synthesized and that an extremely broad repertoire of synthetic organic reactions is available to be potentially employed in synthesizing those compounds. The person skilled in the art knows how to select and implement appropriate synthetic routes. Suitable synthetic methods may be identified by reference to the literature, including reference sources such as *Comprehensive Organic Synthesis*, Ed. B. M. Trost and I. Fleming (Pergamon Press, 1991), *Comprehensive Organic Functional Group Transformations*, Ed. A. R. Katritzky, O. Meth-Cohn, and C. W. Rees (Pergamon Press, 1996), *Comprehensive Organic Functional Group Transformations II*, Ed. A. R. Katritzky and R. J. K. Taylor (Editor) (Elsevier, $2^{nd}$ Edition, 2004), *Comprehensive Heterocyclic Chemistry*, Ed. A. R. Katritzky and C. W. Rees (Pergamon Press, 1984), and *Comprehensive Heterocyclic Chemistry II*, Ed. A. R. Katritzky, C. W. Rees, and E. F. V. Scriven (Pergamon Press, 1996).

IV. Pharmaceutical Compositions

Provided herein are pharmaceutical compositions comprising one or more of the compounds described above. The pharmaceutical compositions provided herein contain one or more compounds of formula (I) in an amount that is useful in the treatment of cancer.

In some embodiments, the pharmaceutical composition further comprises a pharmaceutically acceptable carrier, excipient, or diluent. Pharmaceutical carriers suitable for administration of the compounds provided herein include any such carriers known to those skilled in the art to be suitable for the particular mode of administration. Pharmaceutically acceptable carriers, excipients, and diluents include, but are not limited to, ion exchangers, alumina, aluminum stearate, lecithin, self-emulsifying drug delivery systems (SEDDS) such as d-a-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β-, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of compounds of the formulae described herein. In some embodiments, the carrier, excipient, or diluent is a physiologically acceptable saline solution.

The compositions can be, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers (see, e.g., Ansel Introduction to Pharmaceutical Dosage Forms, Fourth Edition 1985, 126).

The concentration of a compound of formula (I) in a pharmaceutical composition will depend on absorption, inactivation and excretion rates of the compound, the physicochemical characteristics of the compound, the dosage schedule, and amount administered as well as other factors known to those of skill in the art. For example, the amount that is delivered is sufficient to treat colorectal cancer, as described herein. In another embodiment, the amount that is delivered is sufficient to treat prostate cancer. In another embodiment, the amount that is delivered is sufficient to treat pancreatic cancer.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing a compound of formula (I) in the range of 0.005% to 100% with the balance made up from a non-toxic carrier may be prepared. Methods for preparation of these compositions are known to those skilled in the art. The contemplated compositions may contain 0.001%400% active ingredient, in one embodiment 0.1-95%, in another embodiment 75-85%.

V. Methods of Use

Compounds according to formula (I) are therapeutically useful. Accordingly, provided herein are uses of the compounds according to formula (I) in therapy, and therapeutic methods comprising administering a compound according to formula (I), or a pharmaceutically acceptable salt form thereof, to a subject.

The compounds according to formula (I) are effective to treat cancer. Accordingly, provided herein is a method for treating cancer comprising causing an effective amount of a compound according to formula (I), or a pharmaceutically acceptable salt form thereof, to be present in a subject. The causing may be achieved by administering an effective amount of a compound according to formula (I), or a pharmaceutically acceptable salt form thereof, to an individual in need of such treatment, or administering a prodrug of such a compound.

The compounds according to formula (I) are believed to be effective against a broad range of cancers and tumor types, including, but not limited to, bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer.

In some embodiments, cancers that may be treated by the compounds, compositions and methods described herein include, but are not limited to, the following:

cardiac cancers, including, for example, sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel or colon, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenstrom's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue. Thus, the term "tumor cell", as provided herein, includes a cell afflicted by any one of the above identified disorders.

The compounds according to formula (I) can be administered in combination with existing methods of treating cancers, for example by chemotherapy, irradiation, or surgery. Thus, there is further provided a method of treating cancer comprising administering an effective amount of a compound according to formula (I), or a pharmaceutically acceptable salt form thereof, to a subject in need of such treatment, wherein an effective amount of at least one additional cancer chemotherapeutic agent is administered to the subject. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

The compounds according to formula (I) can also be administered to a subject in combination with surgical methods to treat cancers, e.g., resection of tumors. The compounds can be administered to the individual prior to, during, or after the surgery. The compounds can be administered parenterally or injected into the tumor or surrounding area after tumor removal, e.g., to minimize metastases or to treat residual tumor cells present.

The compounds according to formula (I), or a pharmaceutically acceptable salt form thereof, can also be administered with an additional therapeutic agent. In some embodiments, a compound according to formula (I) can be administered in combination with (i.e., before, during, or after) administration of a pain relief agent (e.g., a nonsteroidal anti-inflammatory drug such as celecoxib or rofecoxib), an antinausea agent, or an additional anti-cancer agent.

Also provided herein is a method of promoting cell death. The method includes contacting the cell with a therapeutically effective amount of a compound of formula (I), or a pharmaceutically acceptable salt form thereof. The method of promoting cell death may be performed by contacting the cell with a compound according to formula (I) in vitro, thereby promoting cell death in vitro. Uses of such an in vitro method of promoting cell death include, but are not limited to use in a screening assay (for example, wherein a compound according to formula (I) is used as a positive control or standard compared to compounds of unknown activity or potency in promoting cell death). In some embodiments thereof, the cell death is promoted in a cancer cell.

The method of promoting cell death may be performed, for example, by contacting a tumor cell with a compound according to formula (I), in vivo, thereby promoting cell death in a subject in vivo. The contacting is achieved by causing a compound according to formula (I), or a pharmaceutically acceptable salt form thereof, to be present in the subject in an amount effective to achieve cell death. This may be achieved, for example, by administering an effective amount of a compound according to formula (I), or a pharmaceutically acceptable salt form thereof, to a subject. Uses of such an in vivo method of promoting cell death include, but are not limited to use in methods of treating a disease or condition, wherein promoting cell death is beneficial. In some embodiments thereof, the cell death is promoted in a cancer cell, for example in a subject suffering from cancer. The method is preferably performed by administering an effective amount of a compound according to formula (I), or a pharmaceutically acceptable salt form thereof, to a subject who is suffering from cancer. See Example 2.

VI. Kits

Also provided herein are kits. Typically, a kit includes a compound of formula (I). In some embodiments, a kit can include one or more delivery systems, e.g., for a compound of formula (I), and directions for use of the kit (e.g., instructions for treating a subject). In some embodiments, a kit can include a compound of formula (I) and one or more additional anticancer agents. In some embodiments, a kit can include a compound of formula (I) and one or more antinausea agents. In some embodiments, the kit can include a compound of formula (I) and one or more pain relief agents. In some embodiments, the kit can include a compound of formula (I) and a label that indicates that the contents are to be administered to a subject resistant to an anticancer agent. In some embodiments, a kit can include a compound of formula (I) and a label that indicates that the contents are to be administered with an anticancer agent. In some embodiments, a kit can include a compound of formula (I) and a label that indicates that the contents are to be administered with an antinausea agent. In some embodiments, a kit can include a compound of formula (I) and a label that indicates that the contents are to be administered with a pain relief agent.

EXAMPLES

Example I

Preparation of Compounds II-a, II-b, II-c, II-d, II-e, II-f, and II-g

Bromoacetophenones, either from a commercial source or synthesized by direct bromination of the corresponding acetophenones, were used. The bromination was affected by treating a solution of the acetophenone in dry DMF with elemental bromine in the same solvent and initiating the reaction with catalytic amounts of HBr in acetic acid. The solution was stirred at 37° C. overnight, the solvent was distilled in vacuum, and the residue was purified by column chromatography on silica gel using a 1:1 mixture of hexanes in ethyl acetate.

The bromoacetophenones (2 eq) were dissolved in acetone containing a catalytic amount of sodium iodide and a solution was treated with finely pulverized sodium sulfate (1 eq) and the resulting heterogeneous mixture was vigorously stirred at room temperature overnight. The precipitated solid was filtered off and the acetone was distilled in vacuum. The oily residue was purified by silica gel chromatography using ethyl acetate-graduated hexanes. The resulting diketo sulfide product (1 eq) was reduced to the corresponding diol with diborane (2 eq) at ambient temperature. The synthesis is shown in Scheme 1.

Scheme 1:

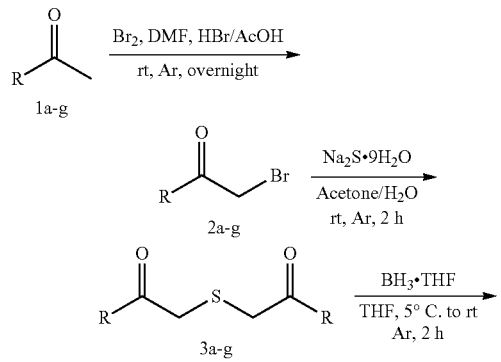

R: a = phenyl
b = 2,3-dimethoxy phenyl
c = 4-trifluoromethoxy
d = 4-trifluoromethyl
e = 3,5-bis(trifluoromethyl)
f = 3,4-dihydroxy phenyl
g = 4-hydroxy-3-methoxy phenyl Example 2

Preparation of Water-Soluble Conjugates
(Compound II-e PEG)

Compound II-e (1 eq) was coupled to PEG disuccinate (SX-PEG-SX, 1 eq) by EDC as a coupling agent using DMAP as a catalyst. The conjugate was purified using size-exclusion chromatography or dialysis. The synthesis is shown in Scheme 2.

Scheme 2:

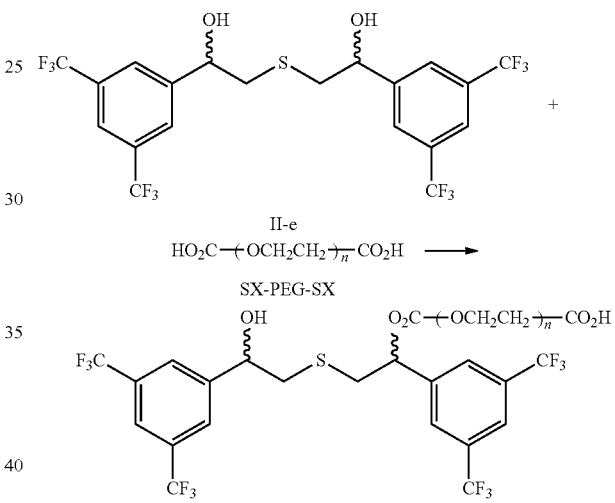

Example 3

Cytotoxicity Screening

Tumor cells were maintained as monolayers in 75-cm$^2$ tissue culture flasks using their respective cell culture medium containing 10% fetal bovine serum and 2 mM L-glutamine. The cells were incubated at 37° C. under a humidified 5% $CO_2$: air atmosphere (standard conditions) for five days. The cells were harvested when in mid-log growth and their concentration was determined using a particle counter (Beckman Coulter, Inc, Fullerton, Calif.). An aliquot of the cell suspension was diluted in culture medium for delivery to a 24-well tissue culture plate at a range of 10,000 to 30,000 per 1 mL per well. After 24 h, quadruplicate wells were inoculated with either vehicle (untreated controls) or test compounds at various concentrations. After 24 h of incubation, the wells were aspirated, washed once with 1 mL PBS, and refilled with 1 mL treatment-free medium. Following a 96-h incubation under the initial treatment conditions, the viable cells were counted and the numbers were normalized to the percent of untreated controls. The extent of cytotoxicity in treated wells as compared to the controls and the dose that inhibits 50% cell proliferation ($IC_{50}$) was calculated. These results are shown in Table 1.

TABLE 1

Inhibition[a] of human cancer cell lines[b] using bis-(2-hydroxy-2-phenylethyl)sulfides

| Compound | Cell Line | | | |
|---|---|---|---|---|
| | LS174-T | MIA PaCa-2 | Panc-1 | PC-3 |
| II-a | NA[c] | NA | NA | 5 ± 9 |
| II-b | 0 | 0 ± 8 | 0 ± 3 | 8 ± 4 |
| II-c | 13 ± 7 | 34 ± 14 | 43 ± 9 | 40 ± 7 |
| II-d | 33 ± 6 | 11 ± 4 | 27 ± 5 | 43 ± 4 |
| II-e | 96 ± 0 | 94 ± 2 | 80 ± 4 | 78 ± 4 |
| | 96 ± 1[d] | 94 ± 2[d] | | |
| | $IC_{50}$ = 3.6 μM[e] | $IC_{50}$ = 3.7 μM | $IC_{50}$ = 6.3 μM | $IC_{50}$ = 4.4 μM |
| II-e PEG | 98 ± 1[f] | NA | NA | NA |
| II-e bis-OAc[g] | NA | 29 ± 6 | NA | NA |
| curcumin | $IC_{50}$ = 6.5 μM | $IC_{50}$ = 9.0 μM | NA | $IC_{50}$ = 12.0 μM |

[a] percent cell death normalized against controls
[b] treatments at 10 μM unless otherwise specified
[c] not as yet available
[d] measured at 7.5 μM
[e] drug dose to inhibit 50% cell proliferation
[f] measured at 5 μM with respect to the drug moiety
[g] 4,4'-thiobis(3-(3,5-bis(trifluoromethyl)phenyl)butan-2-one)

Example 4

Evaluation of Systemic Toxicity

Normal female nude mice were randomized into 2×3 groups and were injected intravenously (iv) with compound II-e at 10 mg/kg (group 1) and 50 mg/kg (group 2). The animals were observed for signs of drug toxicity (morbidity and mortality). As no toxicity was observed by day 3, the dose of group 1 was escalated to 100 mg/kg and the mice were observed for another 31 days. No toxicity was observed.

Example 5

Evaluation of Antitumor Activity

Antitumor activity of compound II-e was evaluated using a nude mouse model of Ls174-T human colon cancer tumors. Female nude mice were implanted subcutaneously (sc) with LS174-T human colon carcinoma cells ($10^7$ cells/mouse). When tumors reached a cross diameter of 7 mm, the mice were randomized into 2×8 groups and were injected iv with either the vehicle (5% dextrose solution containing 20% 50:50, Cremophore EL: ethanol)) or a solution II-e in the same solvent system. The protocol used was qdx5 injections every 24 h. Tumor volumes were monitored by caliper measurement 3× weekly (see FIG. 1 wherein circles correspond to inactivated compound IIe; triangles correspond to vehicle; and squares correspond to compound II-e). Results indicated that compound II-e was able to increase tumor doubling time from 15 days for the untreated control group to 30 days for the compound II-e treated mice (n=8, p=0.043).

A number of embodiments of the invention have been described. Nevertheless, it will be understood that various modifications may be made without departing from the spirit and scope of the invention. Accordingly, other embodiments are within the scope of the following claims.

What is claimed is:

1. A compound according to formula (II-d):

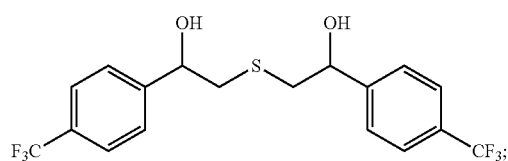 [SMILES: OC(CSCC(O)c1ccc(C(F)(F)F)cc1)c1ccc(C(F)(F)F)cc1]

or a pharmaceutically acceptable salt form thereof.

2. A compound according to formula (II-e):

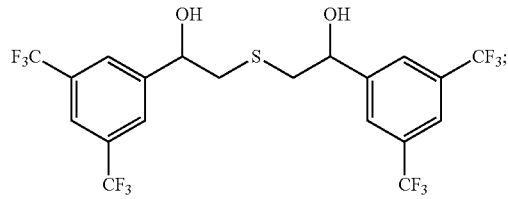 [SMILES: OC(CSCC(O)c1cc(C(F)(F)F)cc(C(F)(F)F)c1)c1cc(C(F)(F)F)cc(C(F)(F)F)c1]

or a pharmaceutically acceptable salt form thereof.

3. A compound according to formula (II-f):

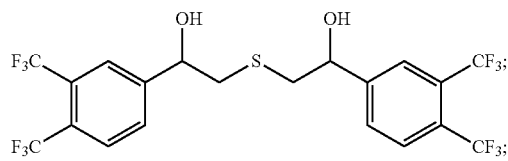 [SMILES: OC(CSCC(O)c1ccc(C(F)(F)F)c(C(F)(F)F)c1)c1ccc(C(F)(F)F)c(C(F)(F)F)c1]

or a pharmaceutically acceptable salt form thereof.

4. A compound according to formula (II-e PEG):
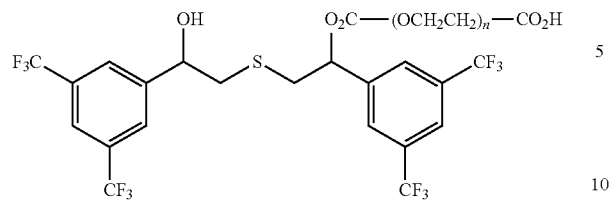
wherein n is an integer from 1 to 1000;
or a pharmaceutically acceptable salt form thereof.
5. A pharmaceutical composition comprising one or more of a pharmaceutically acceptable carrier, excipient, diluent, or adjuvant; and a compound according to any one of claims 1-3 or 4.
* * * * *